(12) United States Patent
Duarte

(10) Patent No.: US 9,095,620 B2
(45) Date of Patent: Aug. 4, 2015

(54) REAGENTS

(75) Inventor: Franco J. Duarte, Huntsville, AL (US)

(73) Assignee: NEKTAR THERAPEUTICS, San Francisco, CA (US)

( * ) Notice: Subject to any disclaimer, the term of this patent is extended or adjusted under 35 U.S.C. 154(b) by 1181 days.

(21) Appl. No.: 12/921,778

(22) PCT Filed: Mar. 12, 2009

(86) PCT No.: PCT/US2009/001558
§ 371 (c)(1),
(2), (4) Date: Dec. 6, 2010

(87) PCT Pub. No.: WO2009/114151
PCT Pub. Date: Sep. 17, 2009

(65) Prior Publication Data
US 2011/0071093 A1 Mar. 24, 2011

Related U.S. Application Data

(60) Provisional application No. 61/069,092, filed on Mar. 12, 2008.

(51) Int. Cl.
*A61K 38/00* (2006.01)
*C07K 16/00* (2006.01)
*A61K 47/48* (2006.01)

(52) U.S. Cl.
CPC ............................... *A61K 47/48215* (2013.01)

(58) Field of Classification Search
CPC ......... C08G 18/73; A61K 45/06; A61K 39/00
See application file for complete search history.

(56) References Cited

U.S. PATENT DOCUMENTS

| | | | |
|---|---|---|---|
| 4,810,646 A | 3/1989 | Jamas et al. | |
| 4,992,540 A | 2/1991 | Jamas et al. | |
| 5,028,703 A | 7/1991 | Jamas et al. | |
| 5,196,438 A | 3/1993 | Martin et al. | |
| 5,413,999 A | 5/1995 | Vacca et al. | |
| 5,484,926 A | 1/1996 | Dressman et al. | |
| 5,585,397 A | 12/1996 | Tung et al. | |
| 5,607,677 A | 3/1997 | Jamas et al. | |
| 5,629,384 A | 5/1997 | Veronese et al. | |
| 5,672,662 A | 9/1997 | Harris et al. | |
| 5,732,490 A | 3/1998 | Hydary | |
| 5,741,495 A | 4/1998 | Jamas et al. | |
| 5,753,652 A | 5/1998 | Fassler et al. | |
| 5,849,911 A | 12/1998 | Fassler et al. | |
| 6,090,250 A * | 7/2000 | Mazzeo et al. ............... 204/451 |
| 6,147,095 A | 11/2000 | Ferry et al. | |
| 6,231,887 B1 | 5/2001 | Gao et al. | |
| 6,436,989 B1 | 8/2002 | Hale et al. | |
| 6,514,953 B1 | 2/2003 | Armitage et al. | |
| 6,765,019 B1 | 7/2004 | Crooks et al. | |
| 6,992,177 B1 | 1/2006 | Hui et al. | |
| 2004/0127689 A1 | 7/2004 | Sigler | |
| 2005/0136031 A1 | 6/2005 | Bentley et al. | |
| 2005/0281781 A1 | 12/2005 | Ostroff | |
| 2007/0004643 A1 | 1/2007 | Shirasaki et al. | |
| 2008/0044438 A1 | 2/2008 | Ostroff et al. | |

FOREIGN PATENT DOCUMENTS

| | | |
|---|---|---|
| EP | 0 580 402 | 1/1994 |
| EP | 0 560 268 | 1/1995 |
| EP | 0 541 168 | 3/1998 |
| FR | 2 773 994 | 7/1999 |
| WO | WO 93/07128 | 4/1993 |
| WO | WO 93/23368 | 11/1993 |
| WO | WO 95/06061 | 3/1995 |
| WO | WO 95/09843 | 4/1995 |
| WO | WO 95/30670 | 11/1995 |
| WO | WO 97/21685 | 6/1997 |
| WO | WO 02/098949 | 12/2002 |
| WO | WO 2005/000360 | 1/2005 |
| WO | WO 2005/124563 | 12/2005 |
| WO | WO 2006/089156 | 8/2006 |
| WO | WO 2008/095841 | 8/2008 |
| WO | WO 2008/112286 | 9/2008 |
| WO | WO 2008/112289 | 9/2008 |

OTHER PUBLICATIONS

Shirasaki et. al (Exploration of orally available calpain inhibitors: Peptidyl α-ketoamides containing an amphiphile at P3 site. Bioorganic & Medicinal Chemistry, 13 (2005) 4473-4484).*

Anzinger, et al., "Solubilizing acid-labile peptide protecting groups", Ange. Chemie, Int. Ed. In English, vol. 18, No. 9, pp. 686-687, (Sep. 1979).

Bachmeier, et al., "Quantitative Assessment of HIV-1 Protease Inhibitor Interactions with Drug Efflux Transporters in the Blood-Brain Barrier", Pharm. Res., vol. 22, No. 8, pp. 1259-1268, (Aug. 2005).

Chen, et al., "Synthesis and Properties of ABA Amphiphiles", J. Org. Chem., vol. 64, pp. 6870-6873, (1999).

Giorgio, et al, "Synthesis and anti-HIV activity of prodrugs derived from saquinavir and indinavir", Antiviral Chemistry & Chemo Therapy, vol. 11, pp. 97-110, (2000).

Gunaseelan, et al., "Synthesis of Poly(ethylene glycol)-Based Saquinavir Prodrug Conjugates and Assessment of Release and Anti-HIV-1 Bioactivity Using a Novel Protease Inhibition Assay", Bioconjugate, Chem., vol. 15, pp. 1322-1333, (2004).

Hammer, et al., "Treatment for Adult HIV Infection: 2006 Recommendations of the International AIDS Society-USA Panel", JAMA, vol. 296, No. 7, pp. 827-843, (2006).

Kempf, et al., "Antiviral and Pharmacokinetic Properties of C2 Symmetric Inhibitors of the Human Immunodeficiency Virus Type 1 Protease", Antimicrob. Agents and Chemotherp., vol. 35, No. 11, pp. 2209-2214, (Nov. 1991).

(Continued)

*Primary Examiner* — James H Alstrum Acevedo
*Assistant Examiner* — Jeanette Lieb
(74) *Attorney, Agent, or Firm* — Mark A. Wilson

(57) ABSTRACT

Oligomeric reagents are provided comprising a moiety of atoms arranged in a specific order, wherein the moiety is positioned between a water-soluble, non-peptidic oligomer and a pharmaceutically active agent. The oligomeric reagents are useful for, among other things, forming oligomer active agent conjugates. Related methods, compositions, preparations, and so forth are also provided.

3 Claims, No Drawings

(56) References Cited

OTHER PUBLICATIONS

McQuade, et al., "A Synthetic HIV-1 Protease Inhibitor with Antiviral Activity Arrests HIV-Like Particle Maturation", Science, vol. 247, pp. 454-456, (Jan. 26, 1990).
Pauwels, et al., "Rapid and automated tetrazolium-based colorimetric assay for the detection of anti-HIV compounds", J. of Virological Methods, vol. 20, pp. 309-321, (1988).
Rouquayrol, et al., "Synthesis and anti-HIV activity of glucose-containing prodrugs derived from saquinavir, indinavir and nelfinavir", Carbohy. Res., vol. 336, pp. 161-180, 2001.
Rouquayrol, et al., "Transepithelial Transport of Prodrugs of the HIV Protease Inhibitors Saquinavir, Indinavir, and Nelfinavir across Caco-2 Cell Monolayers", Pharm. Res., vol. 19, No. 11, pp. 1704-1712, (2002).
Sartore, et al., "Enzyme Modification by MPEG with an Amino Acid or Peptide as Spacer Arms", Appl. Biochem. Biotech., vol. 27, pp. 45-54, (1991).
Wan, et al., "Novel multi-component nanopharmaceuticals derived from poly(ethylene) glycol, retro-inverso-Tat nonapeptide and saquinavir demonstrate combined anti-HIV effects", AIDS Res. and Therp., 3:12, pp. 1-15, (2006).
Center for Disease Control and Prevention, MMWR, vol. 55, No. 31, pp. 841-844, (Aug. 11, 2006).
PCT International Search Report in PCT Patent Application No. PCT/US2009/001558 date of mailing Jul. 20, 2009.
PCT International Preliminary Report on Patentability in PCT Patent Application No. PCT/US2009/001558 date of mailing Sep. 23, 2010.
Enzon Pharmaceuticals, Macromolecular Engineering Technologies, pp. 1-14, (2004).
NEKTAR™—Transforming Therapeutics, Nektar Molecule Engineering: Polyethylene Glycol and Derivatives for Advanced PEGylation, pp. 1-20, Catalog—2003, (Jul. 2003).
NEKTAR™—Transforming Therapeutics, Nektar Advanced PEGylation: Polyethylene Glycol and Derivatives for Advanced PEGylation, pp. 1-24, Catalog—2004, (Jul. 2004).
NEKTAR™—Transforming Therapeutics, Nektar Advanced PEGylation: Polyethylene Glycol and Derivatives for Advanced PEGylation, pp. 1-30, (Catalog 2005-2006).
NOF Corporation, "PEG Derivatives, Phospholipid and Drug Delivery Materials for Pharmaceuticals", pp. 1-46, Catalogue 2003-1st, (Jan. 2003).
NOF Corporation, "PEG Derivatives, Phospholipid and Drug Delivery Materials for Pharmaceuticals", pp. 1-50, Catalogue 2003-2nd, (Mar. 2004).
NOF Corporation, "PEG Derivatives, Phospholipids and Drug Delivery Materials for Pharmaceutical Products and Formulations", pp. 1-59, Catalogue Ver. 8, (Apr. 2006).
Polypure, Products; PEG amines; PEG acids and amino acids; PEG thiols and disulfides; BIOTINS, (Apr. 2004).
Polypure, Products; PEG amines; PEG acids and amino acids; PEG thiols and disulfides; BIOTINS, (Apr. 2005).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Quanta Biodesign, Ltd., Leading innovator, producer and provider of monodisperse discrete PEG™ (dPEG™) derivatives, (Product Catalog), pp. 1-51, (Updated: Jul. 18, 2005).
Quanta Biodesign, Ltd., Leading innovator, producer and provider of monodisperse discrete PEG™ (dPEG™) derivatives, (Product Catalog), pp. 1-51, (Updated: Nov. 17, 2005).
Shearwater Polymers, Inc., Polyethylene Glycol and Derivatives, pp. 1-49, (Catalog—Mar. 1995).
Shearwater Polymers, Inc., Polyethylene Glycol and Derivatives, pp. 1-53, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—Jan. 2000).
Shearwater Corporation, Polyethylene Glycol and Derivatives for Biomedical Applications, pp. 1-17, (Catalog—Jul. 2001).
European Communication corresponding to European Patent Application No. 09 719 764.4 dated Mar. 23, 2011.
Communication dated Dec. 5, 2013 corresponding to European Patent Application No. 09719764.4-1453 / 2262538.
Communication under Rule 71(3) EPC dated Apr. 15, 2014 corresponding to European Patent Application No. 09719764.4-1453.

* cited by examiner

REAGENTS

CROSS REFERENCE TO RELATED APPLICATIONS

This application is a 35 U.S.C. §371 application of International Application No. PCT/US2009/001558, filed Mar. 12, 2009, designating the United States, which claims the benefit of priority under 35 U.S.C. §119(e) to Provisional Application Ser. No. 61/069,092, filed Mar. 12, 2008, both of which are incorporated herein by reference in their entireties.

FIELD OF THE INVENTION

The present invention relates generally to novel oligomeric reagents comprising a particular internal structural orientation, as well as to conjugates of these novel oligomeric reagents. In addition, the invention relates to methods for synthesizing the oligomeric reagents and methods for conjugating the oligomer reagents to active agents and other substances. Moreover, the invention also relates to pharmaceutical preparations as well as to methods for administering the conjugates to patients.

BACKGROUND OF THE INVENTION

Scientists and clinicians face a number of challenges in their attempts to develop active agents into forms suited for delivery to a patient. Active agents that are polypeptides, acid-labile active agents, or agents with low oral bioavailability are often delivered via injection rather than the oral route. In this way, the active agents are introduced into the systemic circulation without exposure to the acidic environment of the stomach. However, delivery of active agents via injection may lead to rapid clearance by kidney and/or liver. Thus, delivery of active agents is often problematic even when these agents are administered by injection.

Some success has been achieved in addressing the problems of delivering active agents via injection. For example, conjugating the active agent to a water-soluble polymer has resulted in polymer-active agent conjugates having reduced immunogenicity and antigenicity. In addition, these polymer-active agent conjugates often have greatly increased half-lives compared to their unconjugated counterparts as a result of decreased clearance through the kidney and/or decreased enzymatic degradation in circulation. As a result of having greater half-life, the polymer-active agent conjugate requires less frequent dosing, which in turn reduces the overall number of painful injections and inconvenient visits to a health care professional. Moreover, active agents that are only marginally soluble often demonstrate a significant increase in water solubility when conjugated to a water-soluble polymer.

Due to its documented safety as well as its approval by the FDA for both topical and internal use, polyethylene glycol has been conjugated to variety of active agents. Despite these successes, conjugation of a water-soluble polymer to an active agent remains challenging. One such challenge is the deactivation of the active agent upon attachment to a relatively long polyethylene glycol molecule. Although a relatively long polyethylene glycol molecule would provide the corresponding active agent-polymer conjugate with greater water solubility, conjugates bearing such long polyethylene glycol moieties have been known to be substantially inactive in vivo. It has been hypothesized that these conjugates are inactive due to the relatively long polyethylene glycol chain, which may "wrap" itself around the entire active agent, thereby blocking access to potential ligands required for activity.

It would be desirable, therefore (among other things), to be able to provide conjugates such that their hydrolysis rates could be "customized." For example, with respect to the typical weekly administration of PEGylated interferon alpha-2a, a slower rate of hydrolysis might provide for even longer periods between administrations. In addition, conjugates having too long of an in vivo half life could be improved by increasing the conjugates' susceptibility to hydrolysis.

Thus, there is a need in the art to provide reagents with different reactivities to expand the possible repertoire of active agent-conjugates.

The present invention seeks to address these and other needs in the art.

SUMMARY OF THE INVENTION

It is an object of the invention to provide an oligomeric reagent comprising the following structure:

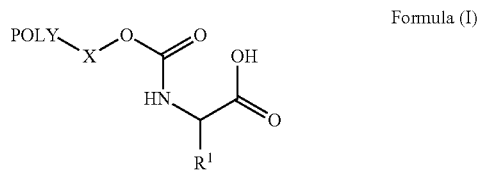

Formula (I)

wherein, $R^1$ is an amino acid side-chain of an alpha-, beta-, or a gamma-amino acid;

X represents a direct covalent bond or a spacer moiety; and

"POLY" is a water-soluble, non-peptidic oligomer.

It is another object of the invention to provide such an oligomeric reagent wherein $R^1$ is tert-butyl.

It is a still another object of the invention to provide an oligomeric reagent wherein the water-soluble, non-peptidic oligomer is a polyethylene glycol or PEG.

It is a still another object of the invention to provide an oligomeric reagent wherein the water-soluble, non-peptidic oligomer is an end-capped polyethylene glycol.

In another object of the invention, end-capped moiety is selected from the group hydroxy, alkoxy, substituted alkoxy, alkenoxy, substituted alkenoxy, alkynoxy, substituted alkynoxy, aryloxy and substituted aryloxy. In another aspect the end-capped group is methoxy.

It is a further object of the invention to provide a method for preparing the above-described oligomeric reagents wherein the method comprises the steps of (i) providing a precursor molecule comprising of a protected reactive group or a precursor to a reactive group; (ii) contacting under covalent coupling conditions the precursor molecule with a water-soluble, non-peptidic oligomer having a hydroxy group, thereby forming an oligomer comprised of a water-soluble, non-peptidic oligomer portion and the protected reactive group; and (iii) reacting the water-soluble, non-peptidic oligomer-precursor with a reagent having a free amino and a free carboxy group.

It is still a further object of the invention to provide an oligomer conjugate

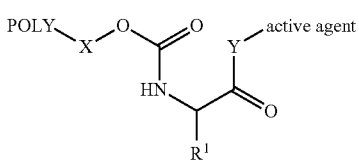

Formula (II)

comprising a water-soluble, non-peptidic oligomer, a reactive moiety, and a pharmacologically active agent (active agent), wherein: (i) the water-soluble, non-peptidic oligomer is linked to the oxygen atom of the $R^1CHNHC(O)O$— moiety through either a direct covalent bond or through a first spacer moiety, X; (ii) the pharmacologically active agent is linked to the carbonyl atom of the $R^1(CO)$— moiety through a direct covalent bond or through a second spacer moiety, Y; and (iii) $R^1$ is an amino acid side-chain of an alpha-, beta-, or a gamma-amino acid.

It is an additional object of the invention to provide a method for preparing a conjugate comprising the step of contacting an oligomeric reagent as provided herein with an active agent under covalent coupling conditions to thereby form the conjugate. Typically, the active agent covalently attaches to the oligomer via reaction between a reactive group on the oligomeric reagent with a functional group (e.g., an amine) on the active agent.

It is still an additional object of the invention to provide a pharmaceutical preparation comprising the active agent-oligomer conjugate as provided herein in combination with a pharmaceutical excipient.

It is an additional object to provide a method for delivering a pharmacologically active agent comprising the step of administering a therapeutically effective amount of an active agent-oligomer conjugate as provided herein.

Additional objects, advantages and novel features of the invention will be set forth in the description that follows, and in part, will become apparent to those skilled in the art upon the following, or may be learned by practice of the invention.

Additional embodiments of the present conjugates, compositions, methods, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION OF THE INVENTION

Before describing the present invention in detail, it is to be understood that this invention is not limited to the particular oligomers, synthetic techniques, active agents, and the like, as such may vary.

It must be noted that, as used in this specification and the claims, the singular forms "a," "an," and "the" include plural referents unless the context clearly dictates otherwise.

In describing and claiming the present invention, the following terminology will be used in accordance with the definitions described below.

"Water-soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble, non-peptidic" oligomer transmits at least 75%, more preferably at least 95%, of the amount of light transmitted by the same solution after filtering. It is most preferred, however, that the water-soluble, non-peptidic oligomer is at least 95% (by weight) soluble in water or completely soluble in water.

The terms "monomer," "monomeric subunit" and "monomeric unit" are used interchangeably herein and refer to one of the basic structural units of an oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with the present invention are homo-oligomers. The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or an oligoethylene glycol is one in which substantially all (preferably all) monomeric subunits are ethylene oxide subunits, though, the oligomer may contain distinct end capping moieties or functional groups, e.g., for conjugation. PEG oligomers for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG oligomers, the variable (n) ranges from about 1 to 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

The terms "end-capped" or "terminally capped" are interchangeably used herein to refer to a terminal or endpoint of a polymer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. In addition, the end-capping group may contain a targeting moiety.

The term "targeting moiety" is used herein to refer to a molecular structure that helps the conjugates of the invention to localize to a targeting area, e.g., help enter a cell, or bind a receptor. Preferably, the targeting moiety comprises of vitamin, antibody, antigen, receptor, DNA, RNA, sialyl Lewis X antigen, hyaluronic acid, sugars, cell specific lectins, steroid or steroid derivative, RGD peptide, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phospatidylglycerol, and phospatidylethanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, and quantum dots.

"Branched," in reference to the geometry or overall structure of an oligomer, refers to an oligomer having two or more oligomer "arms" t extending from a branch point.

"Forked," in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the therapeutic moiety. A composition comprised of monodisperse conjugates may, however, include one or more non-conjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the therapeutic moiety. A composition comprised of bimodal conjugates may, however, include one or more nonconjugate substances such as solvents, reagents, excipients, and so forth.

As used herein, the term "carboxylic acid" is a moiety having a —COOH functional group [also represented as —C(O)OH], as well as moieties that are derivatives of a carboxylic acid, such derivatives including, for example, protected carboxylic acids. Thus, unless the context clearly dictates otherwise, the term carboxylic acid includes not only the acid form, but corresponding esters and protected forms as well. Exemplary protecting groups for carboxylic acids and other protecting groups are described in Greene et al., "PROTECTIVE GROUPS IN ORGANIC SYNTHESIS," Chapter 6, $3^{rd}$ Edition, John Wiley and Sons, Inc., New York, 1999 (p. 454-493). Activated carboxylic acids include but are not limited to acid halides (such as acid chlorides), anhydrides, amides and esters.

As used herein, the term "functional group" or any synonym thereof is meant to encompass protected forms thereof.

The terms "spacer" and "spacer moiety" are used herein to refer to an atom or a collection of atoms optionally used to link interconnecting moieties such as a terminus of a water-soluble, non-peptidic oligomer portion and a functional group. The spacer moiety may be hydrolytically stable or may include a physiologically hydrolyzable or enzymatically degradable linkage.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced. An "alkenyl" group is an alkyl of 2 to 20 carbon atoms with at least one carbon-carbon double bond.

The terms "substituted alkyl" or "substituted $C_{q-r}$ alkyl" where q and r are integers identifying the range of carbon atoms contained in the alkyl group, denotes the above alkyl groups that are substituted by one, two or three halo (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclic, amino, phenoxy, nitro, carboxy, acyl, cyano. The substituted alkyl groups may be substituted once, twice or three times with the same or with different substituents.

"Lower alkyl" refers to an alkyl group containing from 1 to 6 carbon atoms, and may be straight chain or branched, as exemplified by methyl, ethyl, n-butyl, butyl, and t-butyl. "Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion or atom or collection of atoms, which may be ionic, having an electrophilic center, i.e., a center that is electron seeking, capable of reacting with a nucleophile.

"Nucleophile" refers to an ion or atom or collection of atoms, which may be ionic, having a nucleophilic center, i.e., a center that is seeking an electrophilic center or with an electrophile.

The terms "active agent," "biologically active agent" and "pharmacologically active agent" are used interchangeably herein and are defined to include any agent, drug, compound, composition of matter or mixture that provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, these terms further include any physiologically or pharmacologically active substance that produces a localized or systemic effect in a patient.

"Pharmaceutically acceptable excipient" and "pharmaceutically acceptable carrier" refers to an excipient that can be included in the compositions of the invention and that causes no significant adverse toxicological effects to the patient.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g., $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding multivalent moiety, arylene). All atoms are understood to have their normal number of valences for bond formation (i.e., 1 for H, 4 for carbon, 3 for N, 2 for O, and 2, 4, or 6 for S, depending on the oxidation state of the S).

"Pharmacologically effective amount," "physiologically effective amount," and "therapeutically effective amount" are used interchangeably herein to mean the amount of a water-soluble, non-peptidic oligomer-small molecule drug conjugate present in a composition that is needed to provide a threshold level of active agent and/or conjugate in the bloodstream or in the target tissue. The precise amount will depend upon numerous factors, e.g., the particular active agent, the components and physical characteristics of the composition, intended patient population, patient considerations, and the like, and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterodifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein, typically, but not necessarily, in the form of a water-soluble, non-peptidic oligomer-small molecule drug conjugate, and includes both humans and animals.

"Optional" or "optionally" means that the subsequently described circumstance may but need not necessarily occur, so that the description includes instances where the circumstance occurs and instances where it does not.

"Nil" refers to the absence of a substituent group. Thus, when a substituent is nil, the substituent may be represented in the structure as a chemical bond or hydrogen in the resulting structure.

"Multifunctional" in the context of an oligomer of the invention means an oligomer having 3 or more functional groups contained therein, where the functional groups may be the same or different. Multifunctional oligomers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the oligomer backbone. A "difunctional" oligomer means an oligomer having two functional groups contained therein, either the same (i.e., homodifunctional) or different (i.e., heterodifunctional).

A basic or acidic reactant described herein includes neutral, charged, and any corresponding salt forms thereof.

The term "patient," refers to a living organism suffering from or prone to a condition that can be prevented or treated by administration of a conjugate as provided herein, and includes both humans and animals.

An "organic radical" is a carbon-containing moiety that can be attached via a covalent bond to another atom. Exemplary organic radical include those that are selected from the group consisting of alkyl, substituted alkyl, alkenyl, substituted alkenyl, alkynyl, substituted alkynyl, aryl and substituted aryl.

"Optional" or "optionally" means that the subsequently described circumstance may or may not occur, so that the description includes instances where the circumstance occurs and instances where it does not.

As used herein, the "halo" designator (e.g., fluoro, chloro, iodo, bromo, and so forth) is generally used when the halogen is attached to a molecule, while the suffix "ide" (e.g., fluoride, chloride, iodide, bromide, and so forth) is used when the ionic form is used when the halogen exists in its independent ionic form (e.g., such as when a leaving group leaves a molecule).

Turning to a first embodiment of the invention then, a unique oligomeric reagent is provided. Although not wishing to be bound by theory, applicants believe the distinctive properties of the oligomeric reagents described herein are attributable to the unique orientation of atoms. For example, when an oligomeric reagent described herein is coupled to an active agent to form a conjugate, the conjugate's rate of hydrolysis in vivo may be different than the rate of hydrolysis of a conjugate that has the same atoms, but arranged in a different sequence. In addition to providing alternative rates of hydrolysis, the oligomeric reagents provided herein have additional advantages over prior art oligomeric reagents.

Thus, the oligomeric reagent can schematically be represented by the following formula:

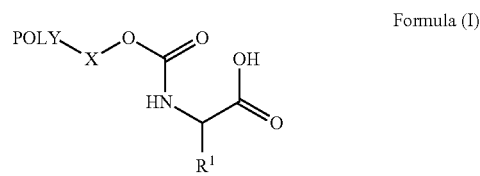

Formula (I)

wherein, $R^1$ is an amino acid side-chain of an alpha-, beta-, or a gamma-amino acid;
X represents a direct covalent bond or a spacer moiety; and "POLY" is a water-soluble, non-peptidic oligomer.

It is still a further object of the invention to provide an oligomer conjugate:

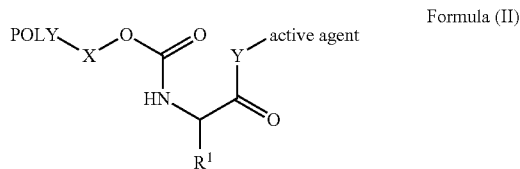

Formula (II)

comprising a water-soluble, non-peptidic oligomer, a reactive moiety, and a pharmacologically active agent, wherein: (i) the water-soluble, non-peptidic oligomer is linked to the oxygen atom of the $R^1$CHNHC(O)O— moiety through either a direct covalent bond or through a first spacer moiety, X; (ii) the pharmacologically active agent is linked to the carbonyl atom of the $R^1$(CO)— moiety through a direct covalent bond or through a second spacer moiety, Y; and (iii) $R^1$ is an amino acid side-chain of an alpha-, beta-, or a gamma-amino acid.

$R^1$ is any generally non-interfering substituent. $R^1$ is H or an organic radical. In those instances when $R^1$ is an organic radical, preferred organic radicals include those selected from the group consisting of alkyl, substituted alkyl, alkenyl, substituted alkenyl, alkynyl, substituted alkynyl, aryl and substituted aryl. Specific examples of preferred organic radicals include those selected from the group consisting of methyl, ethyl, n-propyl, isopropyl, n-butyl, sec-butyl, isobutyl, tert-butyl, n-pentyl, isopentyl, neopentyl, tert-pentyl, and various side chains of alpha-, beta-, and gamma-amino acids. In more preferred embodiments, $R^1$ is an alpha-amino acid side chain, wherein the alpha-amino acid is selected from the group consisting of alanine, asparagine, arginine, aspartic acid, cysteine, glutamine, glutamic acid, glycine, histidine, isoleucine, leucine, lysine, methionine, phenylalanine, proline, serine, threonine, tryptophan, tyrosine, and valine. In another embodiment, $R^1$ is side chain of tert-leucine, i.e., tert-butyl.

With respect to the water-soluble, non-peptidic oligomer, the oligomeric reagents of the invention also comprise at least one water-soluble, non-peptidic oligomer segment. Examples of suitable water-soluble, non-peptidic oligomers include, but are not limited to, poly(alkylene glycols), such as poly(ethylene glycol) ("PEG"), cooligomers of ethylene glycol and propylene glycol having water-solubility, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), such as described in U.S. Pat. No. 5,629,384. In some applications where relatively high water solubility is desired, the water-soluble, non-peptidic oligomer is not poly(propylene oxide).

The water-soluble, non-peptidic oligomer is preferably, although not necessarily, a poly(ethylene glycol) ("PEG") or a derivative thereof. It should be understood, however, that related oligomers are also suited for use in the practice of this invention and that the use of the term "PEG" or "poly(ethylene glycol)" is intended to be inclusive and not exclusive in this respect. Consequently, the term "PEG" includes poly(ethylene glycol) in any of its linear, branched or multi-arm forms, including alkoxy PEG, bifunctional PEG, forked PEG, branched PEG, pendant PEG, or PEG with degradable linkages therein, to be more fully described below.

Use of oligomers (e.g., from a monodisperse or bimodal composition of oligomers, in contrast to relatively impure compositions) to form oligomer-containing compounds may advantageously alter certain properties associated with the corresponding small molecule drug. For instance, a compound of the invention, when administered by any of a number of suitable administration routes, such as parenteral, oral, transdermal, buccal, pulmonary, or nasal, exhibits reduced penetration across the blood-brain barrier. It is preferred that the compounds of the invention exhibit slowed, minimal or effectively no crossing of the blood-brain barrier, while still crossing the gastro-intestinal (GI) walls and into the systemic circulation if oral delivery is intended. Moreover, the compounds of the invention maintain a degree of bioactivity as well as bioavailability in comparison to the bioactivity and bioavailability of the compound free of all oligomers.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, alditol such as mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer can have any of a number of different geometries. For example, the water-soluble, non-peptidic oligomer may be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any water-soluble, non-peptidic oligomers described above.

The molecular weight of the water-soluble, non-peptidic oligomer, excluding the linker portion, is generally relatively low. Exemplary values of the molecular weight of the water-soluble, non-peptidic oligomer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. Thus, for example, when the water-soluble and non-peptidic oligomer includes $CH_3-(OCH_2CH_2)_n-$, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the active agent (in contrast to the step-wise addition of one or more monomers to effectively "grow" the oligomer onto the active agent), it is preferred that the composition containing an activated form of the water-soluble, non-peptidic oligomer be monodisperse. In those instances, however, where a bimodal composition is employed, the composition will possess a bimodal distribution centering around any two of the above numbers of monomers. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., J. Org. Chem., 6870-6873 (1999), WO 02/098949, and U.S. Patent Application Publication 2005/0136031.

As used herein, the term "water-soluble, non-peptidic oligomer" includes those water-soluble, non-peptidic oligomers that are biocompatible and nonimmunogenic and specifically excludes any water-soluble, non-peptidic oligomer segments that are not biocompatible and nonimmunogenic. With respect to biocompatibility, a substance is considered biocompatible if the beneficial effects associated with use of the substance alone or with another substance (e.g., active agent) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the water-soluble, non-peptidic oligomer segments described herein as well as conjugates are biocompatible and nonimmunogenic.

Those of ordinary skill in the art will recognize that the foregoing discussion concerning substantially water-soluble, non-peptidic oligomer is by no means exhaustive and is merely illustrative, and that all oligomeric materials having the qualities described above are contemplated. As used herein, the term "oligomeric reagent" generally refers to an entire molecule, which can comprise a water-soluble, non-peptidic oligomer and a functional group. The term "water-soluble, non-peptidic oligomer" is generally reserved for use in discussing one portion of a larger molecular structure such as an oligomeric reagent, precursor molecule, conjugate, and so forth.

Each portion (e.g., functional group, active agent, water-soluble, non-peptidic oligomer, and so forth) of the oligomeric reagent and other structures described herein can be directly attached to each other via a direct covalent bond. Or it may be attached through a spacer moiety comprised of one or more atoms serving to tether each portion together into a unified whole.

When present, the spacer moiety (through which the water-soluble, non-peptidic oligomer is attached to the active agent moiety) may be a single bond, a single atom, such as an oxygen atom or a sulfur atom, two atoms, or a number of atoms. A spacer moiety is typically but is not necessarily linear in nature. The spacer moieties, generally "X" or "Y," are hydrolytically stable, and are preferably also enzymatically stable. Preferably, the spacer moiety is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

More specifically, in selected embodiments, a spacer moiety of the invention, X, or Y, may be any of the following: "—" (i.e., a covalent bond, that may be stable or degradable, between the active agent residue and the water-soluble, non-peptidic oligomer), —O—, —NH—, —S—, —C(O)—, —C(O)O—, —OC(O)—, —CH$_2$—C(O)O—, —CH$_2$—OC(O)—, —C(O)O—CH$_2$—, —OC(O)—CH$_2$—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—NH—CH$_2$—CH$_2$—CH$_2$—CH$_2$—CH$_2$—, —CH$_2$—C(O)—NH—CH$_2$—CH$_2$—CH$_2$—CH$_2$—, —CH$_2$—CH$_2$—CH$_2$—CH$_2$—C(O)—NH—NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl. Additional spacer moieties include, acylamino, acyl, aryloxy, alkylene bridge containing between 1 and 5 inclusive carbon atoms, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, 4-(methoxy-lower alkyl)-1-piperizinyl, and guanidine. In some instances, a portion or a functional group of the drug compound may be modified or removed altogether to facilitate attachment of the oligomer. In some instances, it is preferred that X is not an amide, i.e., —CONR— or —RNCO—).

For purposes of the present invention, however, a group of atoms is not considered a linkage when it is immediately adjacent to an oligomer segment, and the group of atoms is the same as a monomer of the oligomer such that the group would represent a mere extension of the oligomer chain.

For any given spacer moiety that comprises both a carbonyl and a carbon atom adjacent thereto, the spacer moiety optionally includes an organic radical attached to the carbon atom adjacent to the carbonyl. Conventionally, the carbon atom immediately adjacent to the carbonyl carbon is called the alpha carbon. Thus, an alpha carbon in any given spacer moiety can have an organic radical such as a small alkyl group (e.g., methyl group) attached thereto.

The overall structure of the oligomeric reagent can take any number of different forms. For example, the oligomeric reagent can be linear, branched, multi-armed, dendritic, or forked.

The invention also includes a method for preparing the oligomeric reagents provided herein. The method comprises the step of (i) providing a precursor molecule comprising of a protected reactive group (or unprotected reactive group if such reactive group can remain unaltered when carrying out the method steps) or a precursor to a reactive group and one or more hydroxyl groups. Some precursor molecules that are comprised of a protected reactive group or precursor reactive group and one or more hydroxyl groups can be obtained commercially. In addition, the unprotected forms of the precursor molecule can be synthesized and then protected (if necessary) using conventional techniques.

A method for preparing an oligomeric reagent according to the present invention includes the step of (ii) activating at least one of the one or more hydroxyl groups of the water-soluble, non-peptidic oligomer for reaction with a group to form an activated water-soluble, non-peptidic oligomer. Although any suitable art-known activating reagent can be used, it is preferred to use an activating agent selected from the group consisting of di(N-succinimidyl) carbonate (DSC), N,N'-dicyclohexylcarbodiimide (DCC), N,N'-diisopropylcarbodiimide, N-(3-dimethylaminopropyl)-N'ethylcarbodiimide, 1,1'-carbonyldiimidazole (CDI), 1,1'-carbonyld(1,2,4-triazole) (CDT), bis(4-nitrophenyl) carbonate, p-nitrophenyl chlorocarbonate, p-nitrophenylchloroformate, 4-dimethylaminopyridine (DMAP), phosgene, triphosgene, 1-hydroxybenzotriazole (HOBt), dibenzotriazolyl carbonate (diBTC), N-hydroxysuccinimide and DCC, N-hydroxyphthalimide and DCC, and thiazolidine thione.

Another step of the method for preparing the oligomeric reagents of the invention includes (iii) contacting under covalent coupling conditions at least one of the one or more activated water-soluble, non-peptidic oligomer to a reagent having an amino group (e.g., an amino acid), thereby forming an oligomer comprised of the water-soluble, non-peptidic oligomer portion and the reactive group. Those of ordinary skill in the can determine through routine experimentation which conditions of pH, temperature, and so forth are appropriate for achieving covalent coupling. For example, the coupling step can be conducted several times, each time under a different set of conditions (e.g., different pH's, different temperatures, solvents, and so on). By determining the amount of the oligomer comprised of the water-soluble, non-peptidic oligomer portion and the protected reactive group (by, for example, size-exclusion chromatography) resulting from each set of conditions, it is possible to determine which set(s) of conditions are most appropriate for carrying out the coupling step.

The method of preparing the oligomeric reagents optionally comprises an additional step of isolating the oligomeric reagent once it is formed. Known methods can be used to isolate the oligomer, but it is particularly preferred to use chromatography, e.g., ion exchange chromatography or size exclusion chromatography. Alternately or in addition, the method includes the step of purifying the oligomer once it is formed. Again, standard art-known purification methods can be used to purify the oligomer.

For any given oligomer prepared by the present method, the method advantageously provides the ability to further transform the oligomer (either prior or subsequent to any deprotection step) so that it bears a specific reactive group. Thus, using techniques well known in the art, the oligomer can be functionalized to include a reactive group (e.g., active ester, thiol, maleimide, aldehyde, ketone, and so forth).

The oligomeric reagents described herein are useful for conjugation to biologically active agents or surfaces. Preferred groups suited for reaction with the oligomeric reagents described herein are nucleophilic groups. Exemplary groups include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Such groups suited to react with the oligomeric reagents described herein are known to those of ordinary skill in the art. Thus, the invention provides a method for making a conjugate comprising the step of contacting, under appropriate conjugation conditions, an active agent with an oligomeric reagent described herein.

A biologically active agent for use in coupling to an oligomeric reagent as presented herein may be any one or more of the following. Suitable agents can be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules (preferably insoluble small molecules), peptides, polypeptides, proteins, antibodies, antibody fragments, polysaccharides, steroids, nucleotides, oligonucleotides, polynucleotides, fats, electrolytes, and the like. Preferably, an active agent for coupling to an oligomer as described herein possesses a native amino group, or alternatively, is modified to contain at least one reactive amino group suitable for conjugating to an oligomer described herein.

Specific examples of active agents suitable for covalent attachment include but are not limited to protease inhibitors wherein the protease inhibitor is selected from the group consisting of amprenavir, atazanavir, fosamprenavir, indinavir, lopinavir, saquinavir, nelfinavir, ritonavir, tipranovir and darunavir.

Preferred small molecules for coupling to an oligomer as described herein are those having at least one naturally occurring amino group. Preferred molecules such as these include aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof. In addition, the term "active agent" is intended to encompass the active agent prior to conjugation as well as the active agent "residue" following conjugation.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, maltitol, lactitol, xylitol, sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines, fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethylcellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

In some embodiments of the invention, the compositions comprising the conjugates may further be incorporated into a suitable delivery vehicle. Such delivery vehicles may provide controlled and/or continuous release of the conjugates and may also serve as a targeting moiety. Non-limiting examples of delivery vehicles include, adjuvants, synthetic adjuvants, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), *Rhodotorula* yeast cell particles (YCP). Yeast cells such as *S. cerevisiae* and *Rhodotorula* sp. are preferred; however, any yeast cell may be used. These yeast cells exhibit different properties in terms of hydrodynamic volume and also differ in the target organ where they may release their contents. The methods of manufacture and characterization of these particles are described in U.S. Pat. Nos. 5,741,495; 4,810,646; 4,992,540; 5,028,703; 5,607,677, and US Patent Applications Nos. 2005/0281781, and 2008/0044438.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All non-PEG chemical reagents referred to in the appended examples are commercially available unless otherwise indicated. The preparation of PEG-mers is described in, for example, U.S. Patent Application Publication No. 2005/0136031.

All $^1$H NMR (nuclear magnetic resonance) data was generated by a NMR spectrometer. A list of certain compounds as well as the source of the compounds is provided below.

Example 1

Schematic for Synthesizing the Reagent

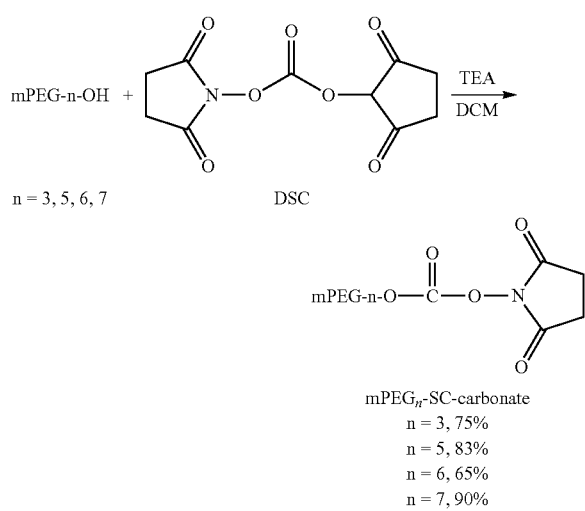

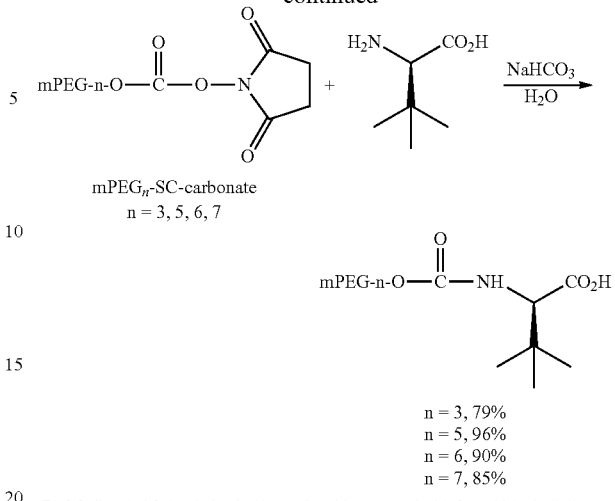

mPEG$_3$-SC-carbonate: Into a 100 mL flask was placed mPEG$_3$-OH (2.0 g, 12.1 mmol) and anhydrous dichloromethane (25 mL). The clear solution was cooled to 0° C., and then triethylamine (1.86 mL, 13.4 mmol, 1.1 equivalents) was added slowly. The solution was stirred for 15 minutes at 0° C., and then was added to a second flask containing a suspension of DSC (3.1 g, 12.1 mmol) in dichloromethane (20 mL). The reaction mixture was allowed to equilibrate to room temperature. After approximately 18 hours, the light-yellow reaction mixture was diluted with dichloromethane (60 mL), transferred to a separatory funnel, and partitioned with deionized water (100 mL). The aqueous layer was extracted with dichloromethane (4×80 mL). The combined organics were washed with water, saturated sodium bicarbonate, and saturated sodium chloride. The dried organic layer was filtered, concentrated under reduced pressure and dried overnight under high vacuum, to give 2.79 g (75%) of mPEG$_3$-SC-carbonate as a light yellow oil. $^1$H NMR (CDCl$_3$) δ 4.40 (m, 2H), 3.80 (m, 2H), 3.70 (bs, 6H), 3.60 (m, 2H), 3.35 (s, 3H), 2.80 (s, 4H); LC/MS=306 (M+1).

mPEG$_5$-SC-carbonate: Into a 100 mL flask was placed mPEG$_5$-OH (2.0 g, 7.92 mmol) and anhydrous dichloromethane (15 mL). The clear solution was cooled to 0° C., and then triethylamine (1.32 mL, 9.51 mmol, 1.2 equivalents) was added slowly. The solution was stirred for 15 minutes at 0° C., and then was added to a second flask containing a suspension of DSC (2.02 g, 7.92 mmol) in dichloromethane (15 mL). The reaction mixture was allowed to equilibrate to room temperature. After approximately 18 hours, the light-yellow reaction mixture was diluted with dichloromethane (40 mL), transferred to a separatory funnel, and partitioned with deionized water (80 mL). The aqueous layer was extracted with dichloromethane (4×50 mL). The combined organics were washed with water, saturated sodium bicarbonate, and saturated sodium chloride. The dried organic layer was filtered, concentrated under reduced pressure and dried overnight under high vacuum, to give 2.59 g (83%) of mPEG$_5$-SC-carbonate as a light yellow oil. $^1$H NMR (CDCl$_3$) δ 4.45 (m, 2H), 3.75 (m, 2H), 3.68 (bs, 16H), 3.55 (m, 2H), 3.34 (s, 3H), 2.80 (s, 4H); LC/MS=394 (M+1).

mPEG$_6$-SC-carbonate: Into a 100 mL flask was placed mPEG$_6$-OH (2.0 g, 6.74 mmol) and anhydrous dichloromethane (12 mL). The clear solution was cooled to 0° C., and then triethylamine (1.12 mL, 8.10 mmol, 1.2 equivalents)

was added slowly. The solution was stirred for 15 minutes at 0° C., and then was added to a second flask containing a suspension of DSC (1.73 g, 6.74 mmol) in dichloromethane (15 mL). The reaction mixture was allowed to equilibrate to room temperature. After approximately 18 hours, the light-yellow reaction mixture was diluted with dichloromethane (50 mL), transferred to a separatory funnel, and partitioned with deionized water (80 mL). The aqueous layer was extracted with dichloromethane (4×50 mL). The combined organics were washed with water, saturated sodium bicarbonate, and saturated sodium chloride. The dried organic layer was filtered, concentrated under reduced pressure and dried overnight under high vacuum, to give 1.92 g (65%) of mPEG$_6$-SC-carbonate as a light yellow oil. $^1$H NMR (CDCl$_3$) δ 4.48 (m, 2H), 3.78 (m, 2H), 3.68 (bs, 20H), 3.58 (m, 2H), 3.38 (s, 3H), 2.84 (s, 4H); LC/MS=438 (M+1).

mPEG$_7$-SC-carbonate: Into a 100 mL flask was placed mPEG$_7$-OH (2.0 g, 5.87 mmol) and anhydrous dichloromethane (15 mL). The clear solution was cooled to 0° C., and then triethylamine (1.22 mL, 8.81 mmol, 1.5 equivalents) was added slowly. The solution was stirred for 15 minutes at 0° C., and then was added to a second flask containing a suspension of DSC (2.25 g, 8.81 mmol) in dichloromethane (15 mL). The reaction mixture was allowed to equilibrate to room temperature. After approximately 18 hours, the light-yellow reaction mixture was diluted with dichloromethane (50 mL), transferred to a separatory funnel, and partitioned with deionized water (80 mL). The aqueous layer was extracted with dichloromethane (4×50 mL). The combined organics were washed with water, saturated sodium bicarbonate, and saturated sodium chloride. The dried organic layer was filtered, concentrated under reduced pressure and dried overnight under high vacuum, to give 2.82 g (90%) of mPEG$_7$-SC-carbonate as a light yellow oil. $^1$H NMR (CDCl$_3$) δ 4.45 (m, 2H), 3.78 (m, 2H), 3.65 (bs, 24H), 3.58 (m, 2H), 3.39 (s, 3H), 2.85 (s, 4H); LC/MS=482 (M+1).

mPEG$_3$-L-tert-Leucine: Into a 125 mL flask was placed L-tert-Leucine (0.43 g, 3.27 mmol) and deionized water (12 mL). The solution was stirred for 30 minutes until clear, followed by the addition of solid sodium bicarbonate (1.27 g, 15.0 mmol, 4.6 equivalents). The cloudy solution was stirred at room temperature, under nitrogen. In a second flask the mPEG$_3$-SC-carbonate (1.24 g, 4.09 mmol, 1.25 equiv.) was taken up in deionized water (12 mL) and this solution was added all at once to the basic L-tert-Leucine solution. The cloudy light-yellow reaction mixture was stirred at room temperature, under nitrogen. After approximately 20 hours, the clear mixture was cooled to 0° C., and carefully acidified with 2 N HCl to pH 1 (20 mL). The acidic mixture was transferred to a separatory funnel and partitioned with dichloromethane (50 mL) and additional water (50 mL). The aqueous layer was extracted with dichloromethane (4×50 mL). The combined organic layers were washed with water and saturated sodium chloride, and dried over sodium sulfate. The dried organic layer was filtered, concentrated under reduced pressure and dried under high vacuum overnight, to give 0.83 g (79%) of mPEG$_3$-L-tert-Leucine as a pale yellow oil. $^1$H NMR (CDCl$_3$) δ 5.45 (d, 1H), 4.26-4.35 (m, 2H), 4.14 (m, 1H), 3.70 (bs, 17H), 3.65 (m, 2H), 3.32 (s, 3H), 0.96 (s, 9H); LC/MS=322 (M+1).

mPEG$_5$-L-tert-Leucine: Into a 250 mL flask was placed L-tert-Leucine (0.68 g, 5.21 mmol) and deionized water (20 mL). The solution was stirred for 30 minutes until clear, followed by the addition of solid sodium bicarbonate (1.96 g, 23.3 mmol, 4.5 equivalents). The cloudy solution was stirred at room temperature, under nitrogen. In a second flask the mPEG$_5$-SC-carbonate (3) was taken up in deionized water (20 mL) and this solution was added all at once to the basic L-tert-Leucine solution. The cloudy light-yellow reaction mixture was stirred at room temperature, under nitrogen. After approximately 18 hours, the clear mixture was cooled to 0° C., and carefully acidified with 2 N HCl to pH 1 (18 mL). The acidic mixture was transferred to a separatory funnel and partitioned with dichloromethane (50 mL) and additional water (50 mL). The aqueous layer was extracted with dichloromethane (4×50 mL). The combined organic layers were washed with water and saturated sodium chloride, and dried over sodium sulfate. The dried organic layer was filtered, concentrated under reduced pressure and dried under high vacuum overnight, to give 2.04 g (96%) of mPEG$_5$-L-tert-Leucine as a pale yellow oil. $^1$H NMR (CDCl$_3$) δ 5.45 (d, 1H), 4.26-4.35 (m, 2H), 4.14 (m, 1H), 3.70 (bs, 17H), 3.65 (m, 2H), 3.38 (s, 3H), 1.02 (s, 9H); LC/MS=410 (M+1).

mPEG$_6$-L-tert-Leucine: Into a 250 mL flask was placed L-tert-Leucine (0.45 g, 3.47 mmol) and deionized water (15 mL). The solution was stirred for 30 minutes until clear, followed by the addition of solid sodium bicarbonate (1.31 g, 15.6 mmol, 4.5 equivalents). The cloudy solution was stirred at room temperature, under nitrogen. In a second flask the mPEG$_6$-SC-carbonate (1.9 gm, 4.34 mmol, 1.25 equiv.) was taken up in deionized water (15 mL) and this solution was added all at once to the basic L-tert-Leucine solution. The cloudy light-yellow reaction mixture was stirred at room temperature, under nitrogen. After approximately 18 hours, the clear mixture was cooled to 0° C., and carefully acidified with 2 N HCl to pH 1 (10 mL). The acidic mixture was transferred to a separatory funnel and partitioned with dichloromethane (50 mL) and additional water (50 mL). The aqueous layer was extracted with dichloromethane (4×50 mL). The combined organic layers were washed with water and saturated sodium chloride, and dried over sodium sulfate. The dried organic layer was filtered, concentrated under reduced pressure and dried under high vacuum overnight, to give 1.39 g (90%) of mPEG$_{6-L}$-tert-Leucine as a pale yellow oil. $^1$H NMR (CDCl$_3$) δ 5.47 (d, 1H), 4.10-4.30 (m, 2H), 4.14 (m, 1H), 3.70 (bs, 20H), 3.65 (m, 2H), 3.38 (s, 3H), 1.02 (s, 9H); LC/MS=454 (M+1).

mPEG$_7$-L-tert-Leucine: Into a 250 mL flask was placed L-tert-Leucine (0.31 g, 2.32 mmol) and deionized water (15 mL). The solution was stirred for 30 min until clear, followed by the addition of solid sodium bicarbonate (0.89 g, 10.6 mmol, 4.5 equivalents). The cloudy solution was stirred at room temperature, under nitrogen. In a second flask the mPEG$_7$-SC-carbonate (1.4 gm, 2.91 mmol, 1.25 equiv.) was taken up in deionized water (15 mL) and this solution was added all at once to the basic L-tert-Leucine solution. The cloudy light-yellow reaction mixture was stirred at room temperature, under nitrogen. After approximately 18 hours, the clear mixture was cooled to 0° C., and carefully acidified with 2 N HCl to pH 1 (8 mL). The acidic mixture was transferred to a separatory funnel and partitioned with dichloromethane (50 mL) and additional water (50 mL). The aqueous layer was extracted with dichloromethane (4×50 mL). The combined organic layers were washed with water and saturated sodium chloride, and dried over sodium sulfate. The dried organic layer was filtered, concentrated under reduced pressure and dried under high vacuum overnight, to give 1.0 g (85%) of mPEG$_7$-L-tert-Leucine as a pale yellow oil. $^1$H NMR (CDCl$_3$) δ 5.46 (d, 1H), 4.10-4.25 (m, 2H), 4.14 (m, 1H), 3.70 (bs, 24H), 3.65 (m, 2H), 3.38 (s, 3H), 1.02 (s, 9H); LC/MS=498 (M+1).

In an alternative scheme, charge 1 g of m-PEG$_6$-succinimidyl carbonate, 0.36 g L-tert-leucine, 10 ml dichloromethane, and 0.4 ml triethylamine to a reactor. Stir for 3 hours. Wash with aqueous hydrochloric acid twice. Dry the organic layer with sodium sulfate. Remove solvent under vacuum. Yield 96.5%.

De Novo Synthesis of PEG-Atazanavir

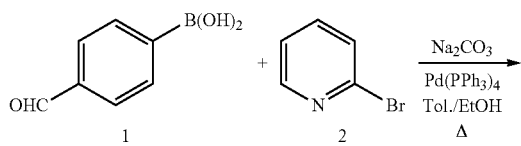

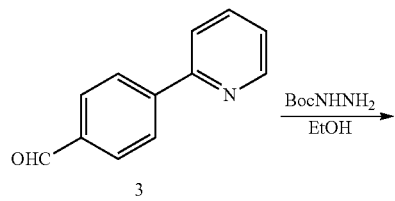

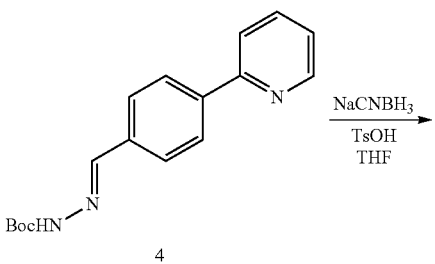

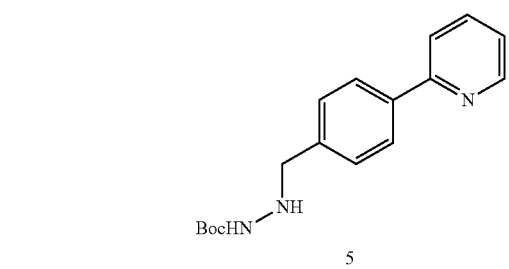

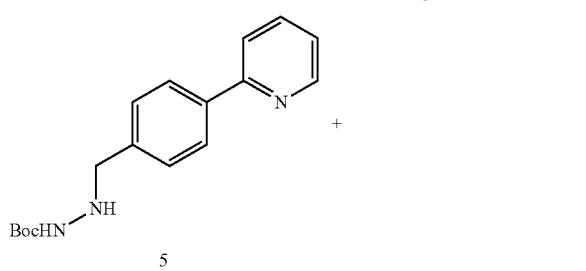

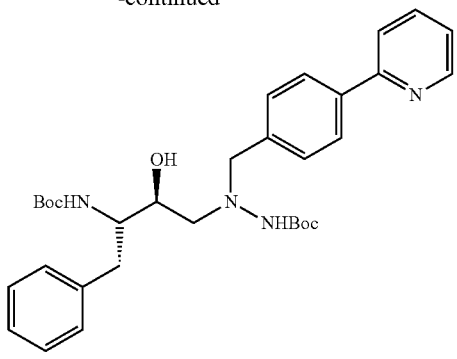

All reactions with air- or moisture-sensitive reactants and solvents were carried out under nitrogen atmosphere. In general, reagents and sovents (except PEG-based reagents) were used as purchased without further purification. Analytical thin-layer chromatography was performed on silica $F_{254}$ glass plates (Biotage). Components were visualized by UV light of 254 nm or by spraying with phosphomolybdic acid. Flash chromatography was performed on Biotage SP4 system. $^1$H NMR spectra: Bruker 300 MHz; chemical shifts of signals are expressed in parts per million (ppm) and are referenced to the deuterated solvents used. MS spectra: rapid resolution Zorbax C18 column; 4.6×50 mm; 1.8 µm. HPLC method had the following parameters: column, Betasil C18, 5-µm (100×2.1 mm); flow, 0.5 mL/minute; gradient, 0-23 minutes, 20% acetonitrile/0.1% TFA in water/0.1% TFA to 100% acetonitrile/0.1% TFA; detection, 230 nm. $t_R$ refers to the retention time. Abbreviations: TPTU, O-(1,2-Dihydro-2-oxo-1-pyridyl)-N, N,N',N'-tetramethyluroniumtetrafluoroborate; DIPEA, N, N'-Diisopropylethylamine.

4-Pyridin-2-yl-benzaldehyde (3): A mixture of 4-formylphenylboronic acid (5.0 g, 33.0 mmol) and 2-bromopyridine (5.53 g, 35.0 mmol, 1.05 equiv.) in 265 mL of 4:3 toluene/95% ethanol was degassed with nitrogen for 30 minutes and then heated under a nitrogen atmosphere, resulting in a clear solution. A slurry of Pd(PPh$_3$)$_4$ (0.77 g) in 50 mL of a 4:4 mixture of toluene and 95% ethanol was added, followed by 50 mL of 3M aqueous Na$_2$CO$_3$. The resulting mixture was gently refluxed at 77° C. After 16 hours, the reaction mixture was cooled to room temperature, and the solid removed by filtration. The filtrate was transferred to a separatory funnel, and the layers separated. The aqueous layer was extracted with toluene (3×50 mL). The combined organics were washed with water, then saturated sodium chloride, and dried over sodium sulfate. The solution was filtered, and the filtrate concentrated under reduced pressure to give a yellow oil. Purification by Biotage chromatography (40+M cartridge; gradient, 0 to 5% methanol/dichloromethane) gave 4.13 g (68%) of (3) as a light-yellow solid. TLC R$_f$(hexane/ethyl acetate, 2:1)=0.25; $^1$H NMR (CDCl$_3$) δ 10.1 (s, HCO), 8.77 (d, 1H), 8.20 (d, 2H), 8.00 (d, 2H), 7.81 (m, 2H), 7.31 (q, 1H); MS (M)$^+$=184; HPLC $t_R$ 1.2 minutes.

N-1-(tert-Butyloxycarbonyl)-N-2-[4-(pyridine-2-yl)benzylidene]-hydrazone (4): To a 100 mL flask was added (3) (0.50 g, 2.73 mmol), tert-butyl carbazate (0.36 g, 2.73 mmol), 2-propanol (3.0 mL) and toluene (3.0 mL). The mixture was heated to reflux (85° C.) under inert atmosphere for two hours, cooled to room temperature gradually and stirred overnight under nitrogen. After 16 hours the reaction mixture was filtered, and the filter cake was washed with a cold mixture of toluene and hexane (1:3; 100 mL). The cake was dried under vacuum to afford 0.73 g (90%) of (4) as an off-white solid. TLC $R_f$ (hexane/ethyl acetate, 1:2)=0.38; $^1$H NMR (CDCl$_3$) δ 8.70 (d, 1H), 8.02 (m, 3H), 7.87 (s, 1H), 7.81 (s, 1H), 7.76 (m, 3H), 7.25 (m, 1H), 1.55 (s, 9H); MS (M)$^+$=298; HPLC $t_R$ 2.1 minutes.

N'-(4-Pyridin-2-yl-benzyl)-hydrazinecarboxylic acid tert-butyl ester (5): Into a 100 mL flask was placed (4) (0.45 g, 1.50 mmol) in THF (3.0 mL). To this solution was added 99% sodium cyanoborohydride (0.12 g, 1.80 mmol, 1.2 equivalents), followed by a solution of p-TsOH (0.35 g, 1.80 mmol, 1.2 equivalents) in THF (3.0 mL). After 1.5 hours, additional p-TsOH (0.35 g, 1.80 mmol, 1.2 equivalents) in THF (3.0 mL) was added. After 16 hours at room temperature, the THF was removed under reduced pressure. The white residue was partitioned between ethyl acetate (35 mL) and water (35 mL). The aqueous layer was extracted with ethyl acetate (3×35 mL). The combined organics were washed with water, then saturated sodium chloride, and then dried over sodium sulfate. After filtration, concentration under reduced pressure, and drying under high vacuum for 6 h, 0.41 g (91%) of (5) was obtained as a white solid. TLC $R_f$ (hexane/ethyl acetate, 1:2)=0.30; $^1$H NMR (DMSO-d$_6$) δ 8.64 (d, 1H), 8.26 (sb, HN), 8.02 (d, 2H), 7.93 (d, 1H), 7.85 (dd, 1H), 7.42 (d, 2H), 7.32 (dd, 1H), 4.80 (m, HN), 3.92 (d, 2H), 1.38 (s, 9H); MS (M)$^+$=300; HPLC $t_R$ 7.0 minutes.

N'-(3-tert-Butoxycarbonylamino-2-hydroxy-4-phenyl-butyl)-N'-(4-pyridin-2-yl-benzyl)-hydrazinecarboxylic acid tert-butyl ester (7): Into a 100 mL flask was placed (5) (1.0 g, 3.34 mmol), (6) (2S,3S)-1,2-epoxy-3-(Boc-amino)-4-phenylbutane (2.78 g, 10.5 mmol, 3.16 equivalents), and 2-propanol (15 mL). The reaction was heated to reflux. After approximately 61 hours of refluxing, the heat was removed, and the mixture cooled to room temperature. To the cooled mixture was added water/ice (50 mL). To the aqueous mixture was added dichloromethane (50 mL) and then transferred to a separatory funnel. The aqueous layer was extracted with dichloromethane (3×50 mL). The combined organics were washed with water, then saturated sodium chloride, and then dried over sodium sulfate. The dried organic solution was filtered, and the filtrate was concentrated under reduced pressure, and then dried under high vacuum overnight. The yellow foam was purified by Biotage chromatography (40+M cartridge; 0 to 5% methanol/dichloromethane over 25 CV) to give 1.24 g (66%) of (7) as a white solid. TLC $R_f$ (hexane/ethyl acetate, 1:2)=0.45; $^1$H NMR (CD$_3$OD) δ 8.60 (d, 1H), 7.88 (m 4H), 7.50 (d, 2H), 7.36 (m, 1H), 7.25 (m, 4H), 7.18 (m, 1H), 3.93 (m, 2H), 3.70 (m, 2H), 3.0-2.6 (m, 4H), 1.33 (s, 9H), 1.30 (s, 9H); MS (M)$^+$=563; HPLC $t_R$ 9.6 minutes.

3-Amino-4-phenyl-1-[N-(4-pyridin-2-yl-benzyl)-hydrazino]-butan-2-ol trihydrochloride (8)

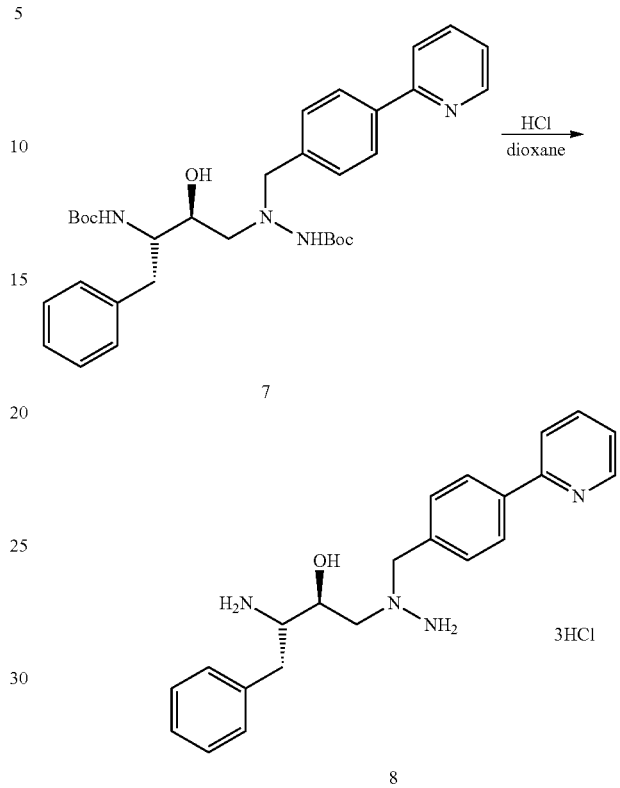

The Boc-aza-isostere (7) (1.2 g, 2.1 mmol) was taken up in 1,4-dioxane (16 mL), and stirred at room temperature, under nitrogen. After five minutes, 4N HCl (12 mL) was added via syringe. There was immediate precipitate formation, and the mixture was stirred at room temperature, under nitrogen. After approximately 18 hours, the dioxane was removed under reduced pressure. The yellow residue was azeotroped with toluene (3×25 mL), and then dried under high vacuum. After 6 hours under high vacuum, 0.92 g (91%) of (8) was obtained as a yellow solid. $^1$H NMR (CD$_3$OD) δ 8.87 (d, 1H), 8.69 (m, 1H), 8.42 (d, 1H), 8.06 (m, 3H), 7.80 (d, 2H), 7.28 (m, 6H), 4.25 (m, 3H), 3.13 (m, 2H), 2.88 (d, 2H); MS (M)$^+$=472.

Synthesis of di-mPEG$_n$-Atazanavir

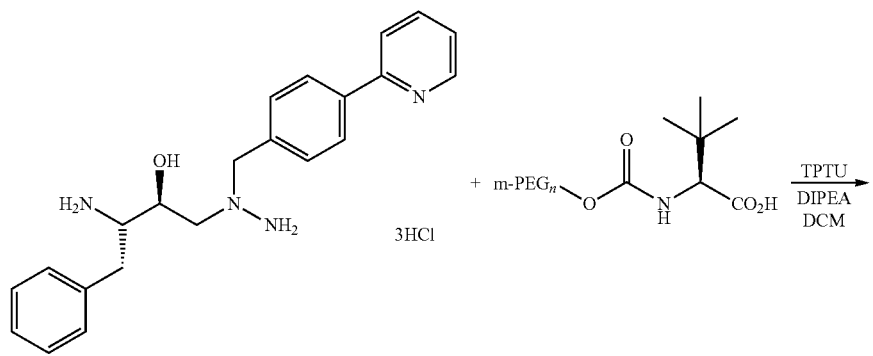

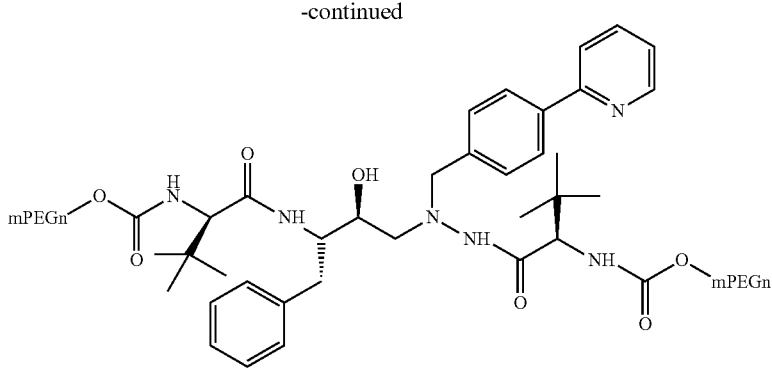

Sythesis of di-mPEG₃-Atazanavir: Into a 100 mL flask was placed mPEG₃-tert-Leucine (0.34 gm, 1.05 mmol, 3.0 equivalents) in anhydrous dichloromethane (3 mL) and cooled to 0° C. Next, TPTU (0.31 gm, 1.05 mmol, 3.0 equiv.), and Hunigs base (0.36 mL, 2.11 mmol, 6.0 equiv.) were added. The cloudy solution was stirred at 0° C. for 15 minutes, and then the diamino backbone trihydrochloride (8) (0.16 gm, 0.35 mmol) was added, as a solid, followed by a dichloromethane rinse (3 mL). The ice bath was removed and the reaction mixture allowed to equilibrate to room temperature. After approximately 20 hours, the reaction mixture was diluted with dichloromethane (20 mL). The mixture was transferred to a separatory funnel, and partitioned with deionized water (50 mL). The aqueous layer was extracted with dichloromethane (4×30 mL). The combined organics were washed with water, saturated sodium bicarbonate, and saturated sodium chloride. The organic layer was dried over sodium sulfate. The drying agent was filtered off, and the filtrate concentrated under reduced pressure to give a yellow oil. Purification was performed using Biotage (40+M cartridge; gradient elution: 0 to 5% methanol/dichloromethane) to give 0.14 gm (45%) of di-mPEG₃-Atazanavir as a clear oil. TLC $R_f$ (5% methanol/dichloromethane)=0.22; ¹H NMR (CDCl₃) δ 8.71 (d, 1H), 7.98 (d, 2H), 7.81 (m, 2H), 7.45 (d, 2H), 7.10-7.30 (m, 10H), 6.22 (d, 1H), 5.35 (d, 1H), 4.25 (m, 4H), 4.01 (m, 4H), 3.50-3.80 (m, 24H), 3.38 (s, 3H), 2.70-3.0 (m, 4H), 0.85 (d, 18H); MS (M)⁺=969; HPLC $t_R$ 7.85 minutes. (96% purity).

di-mPEG₅-Atazanavir: Into a 100 mL flask was placed m-PEG₅-tert-Leucine (2.0 gm, 4.88 mmol, 4.6 equiv.) in anhydrous dichloromethane (10 mL) and cooled to 0° C. Then added TPTU (1.45 gm, 4.88 mmol, 4.6 equiv.), and Hunigs base (1.85 mL, 10.6 mmol, 10.0 equiv.) The cloudy solution was stirred at 0° C. for 15 minutes, and then the diamino backbone trihydrochloride (8) (0.50 gm, 1.06 mmol) was added, as a solid, followed by a dichloromethane rinse (10 mL). The ice was removed and the reaction mixture was allowed to equilibrate to room temperature. After about 20 hours, the reaction mixture was diluted with dichloromethane (40 mL). The mixture was transferred to a separatory funnel, and partitioned with deionized water (60 mL). The aqueous layer was extracted with dichloromethane (4×50 mL). The combined organics were washed with water, saturated sodium bicarbonate, and saturated sodium chloride. The organic layer was dried over sodium sulfate. The drying agent was filtered off, and the filtrate concentrated under reduced pressure to give yellow oil. Purification was performed using Biotage (40+M cartridge; gradient elution: 0 to 5% methanol/dichloromethane) to give 0.70 gm (58%) of di-mPEG₅-Atazanavir as a light-yellow oil. TLC $R_f$ (5% methanol/dichloromethane)=0.23; ¹H NMR (CDCl₃) δ 8.60 (d, 1H), 7.88 (d, 2H), 7.65 (m, 2H), 7.38 (d, 2H), 7.10-7.25 (m, 8H), 6.18 (d, 1H), 5.30 (m, 2H), 4.15 (m, 4H), 3.92 (m, 3H), 3.45-3.65 (m, 40H), 3.30 (s, 3H), 2.65-2.90 (m, 4H), 0.80 (d, 18H); MS (M)⁺=1146; HPLC $t_R$ 7.72 minutes. (98% purity).

di-mPEG₆-Atazanavir: Into a 100 mL flask was placed mPEG₆-tert-Leucine (0.81 gm, 1.78 mmol, 3.0 equiv.) in anhydrous dichloromethane (3 mL) and cooled to 0° C. Next, EDC (0.34 gm, 1.78 mmol, 3.0 equiv.) and HOBT (0.24 gm, 1.78 mmol, 3.0 equiv.) were added. The cloudy solution was stirred at 0° C. for 15 minutes, and then the diamino backbone trihydrochloride (8) was added (0.28 gm, 0.59 mmol), as a solid, followed by a dichloromethane rinse (5 mL). The ice was removed and the reaction mixture was allowed to equilibrate to room temperature. After about 28 hours, the reaction mixture was diluted with dichloromethane (35 mL). The mixture was transferred to a separatory funnel, and partitioned with deionized water (60 mL). The aqueous layer was extracted with dichloromethane (4×50 mL). The combined organics were washed with water, saturated sodium bicarbonate, and saturated sodium chloride. The organic layer was dried over sodium sulfate. The drying agent was filtered off, and the filtrate concentrated under reduced pressure to give yellow oil. Purification was performed using Biotage (40+M cartridge; gradient elution: 0 to 5% methanol/dichloromethane) to give 0.27 gm (40%) of di-mPEG₆-Atazanavir as a clear oil. TLC $R_f$(5% methanol/dichloromethane)=0.17; ¹H NMR (CDCl₃) δ 8.75 (d, 1H), 78.02 (d, 2H), 7.85 (m, 2H), 7.50 (d, 2H), 7.10-7.25 (m, 6H), 6.22 (d, 1H), 5.40 (m, 2H), 4.20 (m, 4H), 4.15 (m, 3H), 3.52-3.70 (m, 48H), 3.38 (s, 3H), 2.75-2.92 (m, 4H), 0.85 (d, 18H); MS (M)⁺=1234; HPLC $t_R$ 7.70 min. (96% purity).

di-mPEG₇-Atazanavir: Into a 100 mL flask was placed mPEG₇-tert-Leucine (2.13 gm, 4.29 mmol, 4.6 equiv.) in anhydrous dichloromethane (10 mL) and cooled to 0° C. Then added TPTU (1.28 gm, 4.29 mmol, 4.6 equiv.), and Hunigs base (1.14 mL, 6.53 mmol, 7.0 equi.) The cloudy solution was stirred at 0° C. for 15 minutes, and then the diamino backbone trihydrochloride (0.44 gm, 0.93 mmol) was added, as a solid, followed by a dichloromethane rinse (10 mL). The ice was removed and the reaction mixture was allowed to equilibrate to room temperature. After about 22 hours, the reaction mixture was diluted with dichloromethane (30 mL). The mixture was transferred to a separatory funnel, and partitioned with deionized water (50 mL). The aqueous layer was extracted with dichloromethane (4×50 mL). The combined organics were washed with water, saturated Na₂CO₃, and saturated NaCl. The organic layer was dried over sodium sulfate. The drying agent was filtered off, and the filtrate concentrated under reduced pressure to give yellow oil. Purification was performed using Biotage (40+M cartridge; gradient elution: 0 to 5% methanol/dichloromethane) to give 0.47 gm (38%) of di-mPEG₇-Atazanavir as a light-yellow oil. ¹H NMR (CDCl₃) δ 8.60 (d, 1H), 7.90 (d, 2H), 7.70 (m, 2H), 7.35 (d, 2H), 7.10-7.25 (m, 8H), 6.12 (d, 1H), 5.30 (m, 2H), 4.10 (m, 4H), 3.92 (m, 3H), 3.50-3.70 (m, 56H), 3.28 (s, 3H), 2.62-2.90 (m, 4H), 0.78 (d, 18H); MS (M)$^+$= 1321; HPLC $t_R$ 7.69 min. (96% purity).

Similarly, other amino acid-containing moieties may also be conjugated to other therapeutic molecules, including, but not limited to, amprenavir, atazanavir, fosamprenavir, indinavir, lopinavir, saquinavir, nelfinavir, ritonavir, tipranovir and darunavir.

What is claimed is:

1. A composition comprising a diamino backbone and an oligomeric reagent, wherein the diamino backbone has the structure

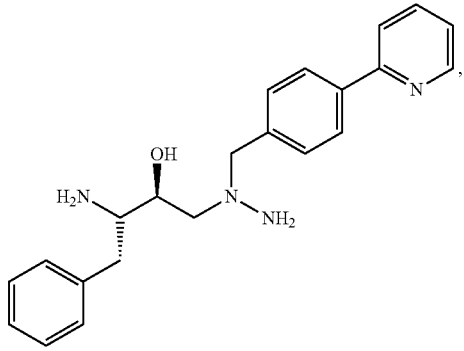

and the oligomeric reagent has the structure-

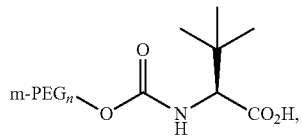

wherein m-PEG is a methoxy-terminated polyethylene glycol.

2. The composition of claim 1, wherein the polyethylene glycol has from about 1 to about 30 ethylene glycol monomers.

3. The composition of claim 2, wherein the polyethylene glycol has from about 1 to about 10 ethylene glycol monomers.

* * * * *